US00PP11989P2

(12) United States Plant Patent
Craig et al.

(10) Patent No.: US PP11,989 P2
(45) Date of Patent: Jul. 17, 2001

(54) REGAL PELARGONIUM PLANT NAMED 'FASCINATION'

(75) Inventors: Richard Craig, State College, PA (US); David G. Clark, Gainesville, FL (US)

(73) Assignee: Penn State Research Foundation, University Park, PA (US)

( * ) Notice: Subject to any disclaimer, the term of this patent is extended or adjusted under 35 U.S.C. 154(b) by 0 days.

(21) Appl. No.: 09/336,499

(22) Filed: Jun. 18, 1999

(51) Int. Cl.[7] ..... A01H 5/00

(52) U.S. Cl. ..... Plt./331

(58) Field of Search ..... Plt./331, 324

*Primary Examiner*—Bruce R. Campell
*Assistant Examiner*—Kent L. Bell
(74) *Attorney, Agent, or Firm*—Webb Ziesenheim Logsdon Orkin & Hanson, P.C.

(57) ABSTRACT

A new and distinct regal Pelargonium having rose pink flowers with deep burgundy upper petals and a scarlet eye on the lower petals with a white center above a mound of medium green foliage. The new cultivar has improved cutting production, rooting speed, and branching and earlier flowering time than 'Fantasy'.

2 Drawing Sheets

BACKGROUND OF THE INVENTION

This discovery relates to a new and distinct cultivar of regal Pelargonium (*Pelargonium×domesticum*) identified by the name of 'Fascination', Breeder No. 93-11-4 and Oglevee, Ltd. No. 978. The cultivar was discovered in an organized, scientifically designed breeding program conducted at the Department of Horticulture, The Pennsylvania State University, University Park, Pa. The new cultivar is the offspring of two unpatented breeding cultivars, Breeder Nos. 87-92-1 (female) and 90-12-5 (male). The floral color and flowering time are similar to the seed parent. The new cultivar's plant habit is not quite as compact as either parent. The purpose of the breeding program was to create new regal Pelargonium genotypes with clear, bright flower colors, excellent propagation characteristics, compact growth habit, predictable and consistent flowering response and good postharvest quality. The new cultivar was produced from prior selections developed at The Pennsylvania State University, University Park, Pa. since 1977. The pedigree of this cultivar includes the patented cultivars 'Splendor' and 'Fantasy' (U.S. Plant Pat. Nos. 7,656 and 7,538, respectively) and other unpatented cultivars as shown in FIG. 2.

The selection was first asexually propagated by cuttings at The Pennsylvania State University and subsequently at Oglevee, Ltd., 152 Oglevee Lane, Connellsville, Pa. The new cultivar reproduces true and been found to retain its characteristics through successive generations.

The new cultivar, when grown in a glass greenhouse in Connellsville, Pa. using full light, 60° F. night temperature, 68° F. day temperature and grown in a soilless media with constant fertilizer at 150–200 ppm nitrogen and potassium, has a response time from a rooted cutting to a flowering plant in a 6 inch pot of fourteen weeks. Rooted cuttings potted Oct. 15, 1997 flowered on Feb. 9, 1998.

DESCRIPTION OF THE DRAWINGS

FIG. 1 depicts a top perspective view of the new cultivar.

DESCRIPTION OF THE PLANT

Figure 2:
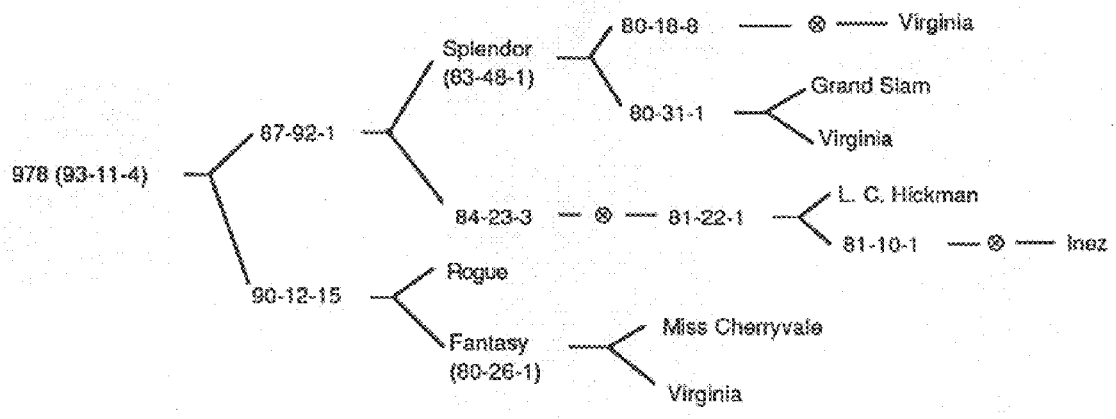
FIG. 2 depicts a flowchart of the pedigree of the new cultivar. Colors depicted in FIG. 1 are as nearly true as is possible with a color illustration of this type.

The following detailed descriptions set forth the characteristics of the new cultivar. The data which define these characteristics were collected from asexual reproductions carried out in Connellsville, Pa. The color readings on a plants grown in a 5 inch pot were taken indoors under 200–220 foot candles of cool white fluorescent light. Color references are primarily to The R.H.S. Colour Chart of The Royal Horticultural Society of London. The data was taken from plants 14 weeks old.

THE PLANT

Classification:
- *Botanical.*—*Pelargonium×domesticum.*
- *Varietal.*—Regal Pelargonium named 'Fascination'.

Form: Medium mound.

Height: 28.0–30.0 cm from soil to top of foliage; 36–40 cm from the soil line to the top of the umbels.

Growth: Medium mound habit with free basal branching; continuous flowering.

Strength: No artificial support needed.

Foliage: Stalked leaf attachment.

Leaves:
- *Size.*—7.9–8.3 cm across.
- *Shape.*—Reniform, truncate base; 7–8.5 cm in length.
- *Margin.*—Serrated, slightly lobed.
- *Texture.*—Leathery, pubescent.
- *Color.*—Top: Green Group 137C. Bottom: Green Group 138B. Zone: None.
- *Ribs and veins.*—Venation: Palmate. Color: Yellow-Green Group 146C.

Petioles:
- *Length.*—6.0–8.0 cm.
- *Color.*—Yellow-Green Group 146C.

Stem:
- *Color.*—Yellow-Green Group 146C.
- *Length.*—6–8 cm.
- *Internode length.*—1.5–2.0 cm.
- *Roots.*—Time to develop: 14–21 days. Description: Fibrous.

THE BUD

Shape: Elliptical cluster; individual bud is elliptical.
Size of umbel: 5.0–5.6 cm across.
Size of bud: 2.5–3.0 cm long and 1.1 cm wide when just showing color.
Color: Yellow-Green Group 146C.

INFLORESCENCE

Blooming habit: Large flowers forming full flower heads.
Borne: Umbel flowers on pedicel, pedicel on peduncle.
Flowers:
*Number of flowers per umbel.*—4–8.
*Umbel depth.*—7.0–8.0 cm.
*Flower depth.*—2.0–3.0 cm.
Open flowers:
*Form.*—Open to slightly cupped; petals overlap, edges ruffled.
*Size of fully open bloom.*—Umbels: 13.5–14.5 cm across. Flowers: 4.5–5.0 cm across.
*Color.*—Top: Upper two petals are White Group 155C at center with veining of Red-Purple Group 64A shading to Greyed-Purple Group 187A then to Red Group 53C with the edge being Red-Purple Group 68D. Lower three petals are White Group 155C at center shading to Red Group 55A then shading to Red-Purple Group 68D at the edge. Bottom: Red Group 65D with veining and eye showing through. Eye: Red Group 52A on upper side of all lower petals.
*Petals.*—5.
*Overall shape.*—Elliptical.
*Apex shape.*—Obovate.
*Base shape.*—Acute.
*Size.*—4.5 cm long; 3.5–4.5 cm wide.
*Texture and appearance.*—Two upper petals appear velvety; appears from a distance as a rose pink/burgundy bi-color flower with prominent eyes on the lower three petals above medium green foliage.
Petaloids: None.
Sepal:
*Size.*—1.0 cm long; 0.5 cm wide.
*Apex shape.*—Acuminate.
*Base shape.*—Truncate.
*Color.*—Yellow-Green Group 144A.
Pedicel:
*Length.*—2.0–3.0 cm.
*Color.*—Greyed-Purple Group 185A over Yellow-Green Group 146C at base of floret with rest of pedicel being Yellow-Green Group 146C.
Peduncle:
*Length.*—6.0–8.5 cm.
*Color.*—Yellow-Green Group 146B.
Disease resistance: None observed.
Lasting quality: Flowers last for 14 to 21 days in the home environment under natural or artificial light.
Natural flowering season: Spring.

REPRODUCTIVE ORGANS

Stamens:
*Anthers.*—4.0 mm long.
*Filaments.*—Length: 1.2–1.9 cm. Color: White.
*Pollen.*—Plentiful.
*Pollen color.*—Golden Orange.
Pistil:
*Number.*—1; five parted.
*Length.*—2.5 cm.
*Stigma color.*—Greyed-Purple Group 187B.
*Style.*—2.0 cm long.
*Ovaries.*—Pale green; 6.0 mm long.
Fruit: None observed.

GENERAL CHARACTERISTICS

Rose pink flowers with deep burgundy upper petals and a scarlet eye on the lower petals with a white center above a mound of medium green foliage. Cutting production, rooting speed, improved branching and earlier flowering time are the improvements over the current market variety 'Fantasy' U.S. Plant Pat. No. 7,538.

We claim:

1. A new and distinct cultivar of regal Pelargonium plant named 'Fascination' substantially as described and illustrated herein.

* * * * *

UNITED STATES PATENT AND TRADEMARK OFFICE

CERTIFICATE OF CORRECTION

PATENT NO. : PP 11,989 P2
APPLICATION NO. : 09/336499
DATED : July 17, 2001
INVENTOR(S) : Craig et al.

It is certified that error appears in the above-identified patent and that said Letters Patent is hereby corrected as shown below:

Title Pg, Col. 1, Ln 1, Insert

-- STATEMENT REGARDING FEDERALLY SPONSORED RESEARCH
This invention was made with government support under
Hatch Act Project Nos. PEN03030 and PEN03393, awarded by the USDA.
The Government has certain rights in the invention. --

Signed and Sealed this

Twelfth Day of August, 2008

JON W. DUDAS
*Director of the United States Patent and Trademark Office*